United States Patent [19]

Hill

[11] Patent Number: 4,793,366

[45] Date of Patent: Dec. 27, 1988

[54] NICOTINE DISPENSING DEVICE AND METHODS OF MAKING THE SAME

[76] Inventor: Ira D. Hill, Clay Court, Locust, N.J. 07760

[21] Appl. No.: 796,883

[22] Filed: Nov. 12, 1985

[51] Int. Cl.⁴ ............................ A24D 1/00; A24F 1/00
[52] U.S. Cl. .................................... 131/273; 131/270; 131/335; 128/202.21
[58] Field of Search ............... 131/235, 332, 331, 270, 131/273; 128/202.21

[56] References Cited

U.S. PATENT DOCUMENTS 4,189,511  2/1980  Levers et al. ........................ 131/332

Primary Examiner—V. Millin
Attorney, Agent, or Firm—Arnold, White & Durkee

[57] ABSTRACT

An improved nicotine dispensing device for non-pyrolytic use which is adapted to release nicotine bearing vapors into air drawn through the device. The device includes a housing and a plurality of microporous polymer filaments which are nicotine loaded. The microporous polymer filaments are characterized by a relatively homogeneous, three-dimensional cellular microstructure. The microporous polymer filaments are made from materials which are selected from olefinic polymers, condensation polymers, oxidation polymers and combinations thereof.

28 Claims, 1 Drawing Sheet

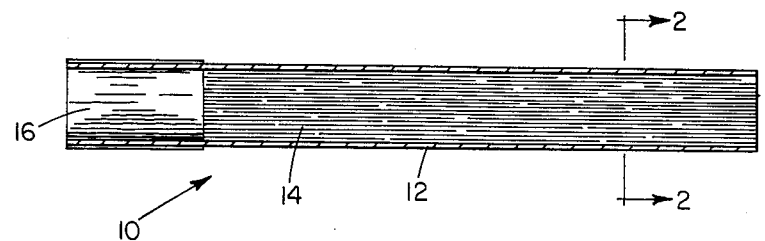
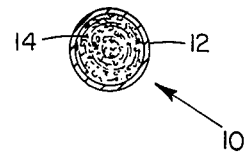
FIG. 1  FIG. 2
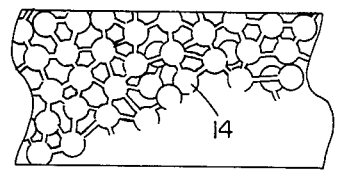
FIG. 3
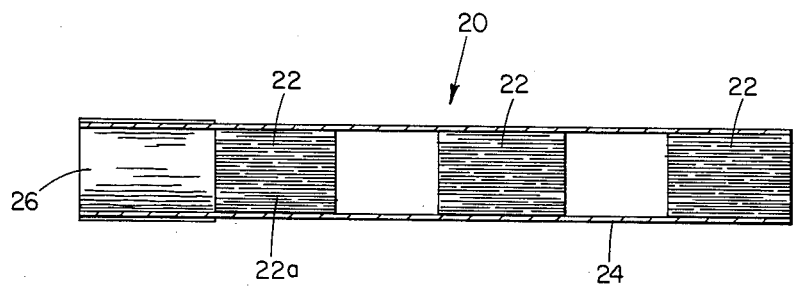
FIG. 4
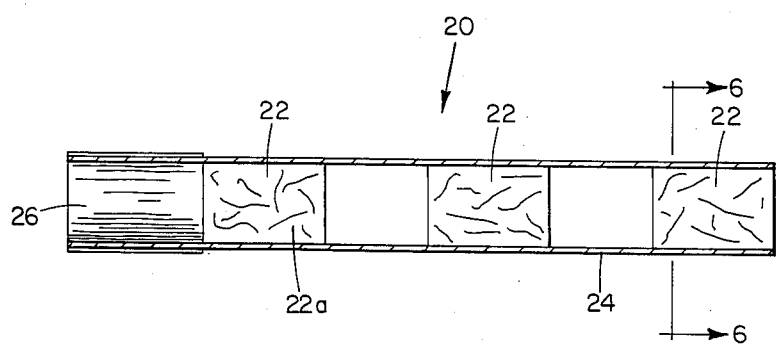
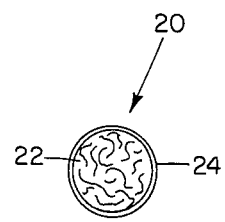
FIG. 5  FIG. 6

NICOTINE DISPENSING DEVICE AND METHODS OF MAKING THE SAME

BACKGROUND OF THE INVENTION

This invention relates to non-combustible nicotine dispensing devices designed to reduce or eliminate the disadvantages associated with conventional smoking habits.

Nicotine is a liquid alkaloid having the empirical formula $C_{10}H_{14}N_2$. When nicotine is obtained from tobacco, as by chewing, sniffing or smoking the substance, the amount of nicotine absorbed into the body generally does not build up to a harmful dose, but produces certain pleasurable effects, frequently leading to habitual use.

One of the most popular versions of nicotine use involves the smoking of cigarettes. When the tobacco in a conventional cigarette is ignited, the combustion of the processed tobacco leaves within the cigarette causes the release of vaporous nicotine, which is drawn through the cigarette and into the user's mouth and lungs when the user sucks or inhales air through the cigarette.

The relative mildness of a cigarette, as compared to a pipe or cigar, permits a user to draw the smoke from the burning cigarette directly into the lungs. Nicotine in the cigarette smoke is rapidly assimilated into the bloodstream of the user from the lungs, so that cigarette smoking provides a method by which a user may very quickly feel the effects of the nicotine.

Although nicotine may be readily introduced into the body through cigarette smoking, the combustion of the tobacco, with the consequent elevated temperatures required in this process, unfortunately results in a number of undesirable consequences associated with smoking combustible cigarettes. Of primary concern are the serious health hazards thought by many to result from smoking combustible cigarettes. Although the nicotine content of a cigarette is not believed to cause serious adverse long-term health effects on the human body, other components are present in tobacco smoke which are thought by many to be harmful. Some of these other constituents appear to be carcinogenic.

Furthermore, the smoking of combustible cigarettes may pose a significant fire hazard. Many fires which have occurred both within buildings or in natural environments have been attributed to carelessly discarded burning cigarettes. In addition, substantial economic losses may be attributed to smoking, including, for example, significant damages to business and personal property resulting from burns in clothing, carpeting, furniture, etc. caused by stray ashes from cigarettes. Cigarette smoking has also become increasingly objectionable because of the discomfort it may cause to non-smokers who are exposed to the smoke and odor produced by practitioners of the smoking habit.

Because of these undesirable side effects of combustible cigarette smoking, attempts have been made from time to time to provide an acceptable substitute for combustible cigarette smoking which eliminates or ameliorates some or all of the adverse consequences mentioned above. Tobacco concentrates, for example, have been processed into a tablet form which may be sucked or chewed, the nicotine being absorbed into the user's body through the lining of the mouth and digestive system. Such a tablet, of course, does not provide the user with the feel of a cigarette held between the lips.

Furthermore, a tablet-type smoking substitute cannot provide the user with an opportunity to draw air and vapors into the mouth nor inhale the air and vapors into the lungs, these actions being a part of the conventional smoking habit. These actions or activities constitute an important aspect of the psychological and physiological affinities which a smoker acquires for the habit. Without an effective substitute for such smoking activities, a smoking substitute is less likely to satisfy the smoker and may thus result in the smoker's return to combustible cigarette smoking.

An important step forward in the development of a smoking substitute is described in U.S. Pat. No. 4,284,089 to Ray, assigned to the assignee o the present invention. In this patent a smokeless device for dispensing nicotine is described which may take the appearance of a conventional smoking item such as a cigarette. Moreover, the device disclosed in that patent enables nicotine to be dispensed in response to users action that closely simulates conventional smoking activity.

In an illustrated embodiment, the Ray patent discloses a device having the general configuration of cigarette. However, the interior of the device defines a gas flow passageway with a flow restriction. The flow restriction is defined by an absorbent material carrying a nicotine solution on the material. In response to the fluid velocity developed at the restriction, nicotine is vaporized from the absorbent material and inhaled by the user. As a result, the user attains a nicotine induced sensation quite similar to that obtained by smoking conventional cigarettes.

While it may be safely posited that the Ray patent represents a pioneering advance in the art, the inventor of the present invention has appreciated that it would be desirable to optimize the performance of a device of the type disclosed in the Ray patent. Particularly, the present inventor has appreciated that it would be highly desirable to increase the amount of nicotine that is vaporized in response to a given puff on such a device.

It is also very important in a device of this kind to efficiently vaporize the nicotine. Liquid nicotine has an extremely bitter, almost caustic taste. Thus, it is important to dispense the nicotine in fashion which encourages vaporization while preventing inadvertent suction of unvaporized droplets, even those of very small size, commonly called an aerosol.

The present inventor has also appreciated that it is important that the nicotine be dispensed in relatively uniform dosages over the life of the product. Unless the user can depend on a steady dosage of nicotine, the use of the dispensing device may be considered less enjoyable than smoking tobacco. Furthermore, it is important for the user to easily determine when the product is depleted which is the case when nicotine delivery is regular prior to exhaustion.

Finally the present inventor appreciated that the above described objectives are most advantageously achieved with a device having a "draw" similar to that of a conventional smoking device, such as a cigarette. It is believed that users may rapidly become dissatisfied with a smoking substitute that requires too little or, more particularly, too much inhalation effort for the sensation achieved. Similarly if the device dispenses too high a nicotine dosage with each puff, the user may receive more nicotine than desired and may be forced to change smoking habits. Either of these alternatives is undesirable in that the user will be less willing to substitute the smokeless substitute if the "familiar feeling" is compromised or if the substitute is somehow less pleasurable.

SUMMARY OF THE INVENTION

In accordance with one preferred embodiment of the present invention the nicotine dispensing device of this invention includes a housing defining a passageway for air and containing a material which holds nicotine. Such a device may include a microporous polymer material in the housing loaded with a nicotine-bearing fluid. In certain embodiments of this invention loaded microporous polymer filaments are interspersed with inert fibers and are arranged in a fashion which permits the design of a device which is similar in style and appearance to a conventional combustible cigarette. In other embodiments the material may take the form of a microporous film or particles.

BRIEF DESCRIPTION OF THE DRAWINGS

Additional objects, features and advantages of the present invention will become apparent by referring to the following detailed description of the preferred embodiments in connection with the accompanying drawings, wherein like reference numerals refer to like elements throughout all the figures. In the drawings:

FIG. 1 is a side elevation in longitudinal section which illustrates one embodiment of a nicotine dispensing device constructed according to the present invention.

FIG. 2 is a cross-sectional view of one embodiment of a nicotine dispensing device of this invention taken along line 2—2 in FIG. 1.

FIG. 3 is a schematic representation in longitudinal section of a microporous polymer filament used in the preferred embodiment of this invention.

FIG. 4 is a side elevation in longitudinal section which illustrates another embodiment of nicotine dispensing device of this invention.

FIG. 5 is a cross-sectional view of one embodiment of a nicotine dispensing device of this invention taken along line 5—5 in FIG. 4.

FIG. 6 is a cross-sectional view of one embodiment of a nicotine dispensing device of this invention taken along line 6—6 of FIG. 5.

DESCRIPTION OF THE PREFERRED EMBODIMENTS

The nicotine dispensing device of this invention includes a housing which contains a porous polymer material loaded with a nicotine-bearing fluid, the device and housing being adapted to release nicotine-bearing vapors into air passing therethrough. In the most preferred embodiment of this invention the housing is in the form of an elongated tube which defines a passageway for air through the nicotine dispensing device. The device is substantially shown by the schematic view appearing as FIG. 1. The nicotine dispensing device of this invention in its most familiar combustible cigarette design format is shown by the numerical designation 10. It should however be understood that other designs and forms are equally viable. The combustible cigarette format illustrated by FIG. 1 is the most conventional configuration of the device but not the only functionally effective form of the device.

The housing may be made of a variety of materials. It is of assistance if the housing 12 material is chemically inert with respect to the nicotine-bearing fluid which is retained by the polymer material.

In the most preferred embodiment of this invention the housing 12 is manufactured with a diameter, length and weight which approximate the size of a conventional combustible cigarette. Furthermore, the housing 12 may be provided with the appropriate color to present the same appearance as a conventional combustible cigarette. In addition, a band 14 made of paper, cork or other suitable material may be applied around the mouthpiece 16 of the device 10 to simulate the appearance of the filter tip on a conventional cigarette.

In other instances it may be desirable to use the actual fitter end of conventional combustible cigarettes. There are several conventional low tar cigarettes on the market which have filters generally made from inert porous polymer materials. Since there is no combustion, the actual filtration mechanism is not strictly necessary. However, in certain instances the end user may desire the appearance, taste or feel of a conventional combustible cigarette filter.

A nicotine-bearing mixture may be dispersed in and dispensed from the polymeric material. It has been found that a number of substances may be advantageously provided in the nicotine mixture which is placed in the nicotine retention means of the present invention. Nicotine (d), nicotine (l) and nicotine (dl) may all be used to advantage in the nicotine-bearing mixture of the present invention to provide the nicotine vapors which are inhaled by the user. A product obtained commercially from Eastman Company, Stock No. 1242, having 98% nicotine (1), has been used in one embodiment of the device and found to perform with satisfactory results.

Any number of nicotine-bearing mixtures are usable for emplacement in the nicotine retention means of the present invention. The specific nicotine-bearing mixture being used in a particular embodiment is largely dependent upon the specific dispensing device, device configuration and substances which are to be dispensed. In the most preferred embodiment of this invention, a number of other materials have been found to provide advantageous results when added to the nicotine bearing mixture. The commercial nicotine which is available in the marketplace is entirely a byproduct of the tobacco industry. Extraction and purification procedures are generally well known in the tobacco industry.

In the nicotine-bearing mixture, nicotine enhancing materials, anti-oxidant and volatile and non-volatile carriers may be added and mixed in accordance with normal manufacturing procedures. It should be noted in selecting additive materials, that they must be suitable for human exposure and/or consumption. In particular, most chemicals may be theoretically toxic if their level of concentration is increased enough. Therefore, it is essential to select the materials for use in the formulation of this invention such that they can be used within accepted toxicity guidelines.

In addition to the above, a number of other materials have been found to provide advantageous results when added to a nicotine-bearing mixture. For example orange oil obtained from commercial orange extract or similarly obtained lemon oil enhance the flavoring of the vapor produced from the nicotine-bearing mixture when added to the nicotine mixture. Such flavorings may also be added in the form of synthetic ingredients. Other flavors which may be advantageously used in the dispensing device include spearmint, peppermint and cinnamon. Of particular value are flavor components extracted from tobacco and a variety of commercially available tobacco fluids and flavor enhancers.

Menthol may also be added to the mixture for a variety of reasons including flavoring or as a carrier material or to suit the particular taste of the user. The menthol which has been used is USP Levoratory, obtained from the Gentry Corporation and is dissolved in ethanol or other solvents to form a liquid. In addition, water may be added to the nicotine formulation. The water vapor which thus evaporates into the air reduces the slight feeling of dry mouth which may be experienced after prolonged use of a dispensing device without the addition of such water.

As described above, it is desirable to provide an optimally volatile and absorbable nicotine molecule which is facilitated by enhancing the nicotine molecule with a complexing substance. The vaporized enhanced nicotine moiety will typically bypass the buccal mucosa and make its way into the lungs where it can be absorbed by the lung tissue and therefore be passed more directly into the blood stream flowing directly to the brain. The pleasurable effect of this is more dramatic than if the nicotine is absorbed through the buccal mucosa and forced to go through the digestive system prior to transmission to the blood stream and eventually the brain. This enhancement represents a significant step forward in the formulation of a nicotine dispensing device. One of the advantages of this enhancement is that by causing the nicotine to be absorbed by the lung tissue, smaller amounts of nicotine can be used to generate the same pleasurable effect.

Finally, it is necessary to have a carrier material in which the nicotine can be vaporized. Suitable carriers include Freon, alcohols, ethers, menthol, methyl salicylate, or other known carrier media. Again, it is necessary that the particular carrier material and the concentration of the particular carrier material be appropriate for human exposure. The concentration of nicotine in the overall nicotine-bearing mixture may be from 1% to 90% by weight and the mixture is usually a fluid. Since some of the carrier evaporates when the mixture is loaded into the device, it is estimated that the concentration of nicotine in the mixture held on the polymer material may advantageously be in the range of from 5 to 100% nicotine by weight.

A variety of flavoring materials may be conveniently added to the formulation to the nicotine bearing fluid mixture to provide a desired effect. As has been previously mentioned, well known flavorants which are approved for human consumption can be used in specified amounts. The use of such flavor materials is not intended to be a limiting factor in this application, but rather, it is intended to recite several of the possibilities for enhancing the final nicotine formulation of this invention.

The polymer material is loaded with the nicotine-bearing mixture or fluid using any conventional technique for combining a liquid and an absorbent medium. Among the suitable techniques are: dipping the polymer material in a bath of the nicotine-bearing mixture; and spraying the nicotine-bearing mixture onto the polymer material. Even after loading, the polymer material feels dry to the touch. This apparent dryness is a result of the nicotine-bearing fluid or mixture being retained within the microporous structure of the polymer and having only limited accesses or gates to the atmosphere. This access limitation provides a number of significant advantages to the nicotine dispensing device of the present invention. The most specific advantage is the unavailability of the nicotine in liquid form. Instead, only nicotine vapors can escape from the microporous polymer filament "gates". Therefore, the user is protected from exposure to the harsh, bitter taste of liquid nicotine. Since nicotine may be toxic at relatively low dosages, the use of the microporous polymer material provides a significant safety advantages.

For purpose of the present invention the polymer material should be sufficiently absorbent of nicotine to hold enough nicotine so that at least about 1 microgram is dispensed in response to each puff of the user. The polymer material is typically made from materials generically described as olefinic polymers, condensation polymers, oxidation polymers and combinations thereof. More specifically, the polymer materials may be made from polymers such as polypropylene, polyvinyl chloride, polyethylene, polymethylpentene, polyethylene-acrylic acid, polyphenylene oxidene and combinations thereof.

The polymer material may take a wide variety of physical configurations. The material may take the form of continuous or noncontinuous filaments of any conventional configuration, flexible films, formed shapes or blocks or even rigid shapes. Composites made of combinations of these configurations and composites of microporous and non-microporous structures may also be utilized.

In practice the loaded polymer material may be arranged in the housing in parallel fashion such as is shown by the embodiment described and shown in FIG. 1. In alternate embodiments of this invention the loaded fibers may be arranged in a random fashion in specific sections of a housing as is shown more particularly by FIG. 3.

In one preferred embodiment of this invention as illustrated by FIG. 1 the microporous polymer filaments are arranged in substantially parallel fashion and retained by the first portion of the housing. Depending on the concentration of the nicotine bearing fluid and the desired nicotine delivery rate in the nicotine dispensing device one or more inert filaments are interspersed with the loaded microporous polymer filaments. The inert fiber materials are manufactured in accordance with well-known and established manufacturing techniques and are typically referred to as "tow".

An important element of the nicotine dispensing device of the present invention is the polymeric material. The use of this material represents a significant advance in nicotine delivery systems. The nicotine-bearing fluid of this invention, when incorporated into the micro-sized reservoirs of the polymeric material, is trapped such that only the vapors can escape through the micro-sized, i.e. in the order of 0.05 to 0.10 microns, gate from the internal pores of the polymer to the atmosphere. The appearance of the microporous polymers of this invention are shown schematically in FIG. 3. It should be understood that this is merely a schematic representation and that in actual practice the microporous structures are available in a variety of configurations.

The microporous materials can be defined as a collection of holes or cells surrounded by a solid outer material, typically referred to as the matrix. Open cell porous materials have holes that are interconnected. If the cells in interconnecting pores are small enough, namely between 0.2 and 100 micrometers, the material is said to be microporous. One preferred microporous polymeric material, sold by Van Leer (UK) Ltd., of Dorset, England, is the Valmic brand polypropylene microporous film. This film is flexible and heat weldable. It has a pore size of from 0.2 micrometers to 3 micrometers with a nominal thickness of about 100 micrometers and a 30% void volume. Another preferred polymeric material sold by Akzona, Inc., Chicago, Ill., made up of microporous polymer filaments is sold under the trademark Accure.

The microporous polymers which are most useful in the improved nicotine dispensing device of this invention are microporous structures of essentially spherical, interconnected void spaces. The void volumes typically range from about 50% to about 85%. Typical pores have a median size of from about 0.10 micrometers to about 10 micrometers. The median cell size is from about 1 micrometer to about 30 micrometer. These specific cell size specifications will control space related characteristics such as capacity and density. Pore size specifications will influence transport properties.

It is possible to directly load active ingredients such as the nicotine-bearing fluid of this invention directly into the microporous polymer matrix. The amount of nicotine-bearing liquid that can be contained by the microporous matrix depends primarily on the void volume fraction of the polymer matrix and the specific gravity of the fluid which is being loaded.

The ease of loading the microporous structures depends on the characteristics of the liquid to be loaded. Liquids with low viscosity surface activity that wet the polymer readily such as acetone, Freon or lower alcohols and lower paraffins may be sprayed or added slowly to the microporous structure. More viscous liquid and low melting solids can be loaded at elevated temperatures. In general, solutions of active substances are readily loaded. The active substance remains in the matrix when the carrier solvent is evaporated. A variety of techniques are available for loading microporous polymers both during extrusion into filament or film form or after extrusion and evaporation of the forming solvent.

As shown in FIGS. 1 and 2, a dispensing device 10, conveniently having the shape and appearance of a cigarette includes a housing 12, a tubular film 14, and a flow restrictor 16. As described previously a wide variety of materials may be used for the housing 12; however, it is preferred to use a material that provides a liquid barrier such as plastic film.

The tubular film 14 carries the nicotine bearing material. Thus, the size of the film 14 may be varied to adjust the dosage of nicotine dispensed. Conveniently the film 14 is secured to the housing 12 by spot welds or glue spots. The axial alignment of the film 14 decreases the exposure of the user to the nicotine-bearing liquid.

The flow restrictor 16 may take a variety of configurations including those shown in U.S. Pat. No. 4,284,089, which is hereby expressly incorporated by reference. In addition to venturi style flow restrictors, flow restrictors having a plurality of restricted paths may be used as well. For example a fibrous tow or plug may be inserted within the film 14 to increase the air flow across the film 14.

As shown in FIGS. 4 and 5, a nicotine dispensing device 20 may include polymeric material in the form of a series of plug 22 of microporous filaments. The plugs 22 may be spaced from one another along the length of the housing 24 and from the mouth piece 26. Appropriate spacers may be included, if desired. The spacing of the plug 22a from the mouth piece 26 helps to reduce the suction of globules of nicotine.

The plugs 22 may take the form of a jumbled ball of microporous filaments as schematically shown in FIG. 5 or the plugs 22 may be formed of combed or aligned filaments as schematically shown in FIG. 4. If desired, the plugs 22 may be joined of a mix microporous filaments and non-microporous filaments or "filler".

Although one or more typical embodiments of the present invention has been illustrated and discussed herein, numerous modifications and alternative embodiments of the apparatus and method of this invention will be apparent to those skilled in the art in view of this description. Accordingly, this description is to be construed as illustrative only and is provided for the purpose of teaching those skilled in the art the manner of constructing the apparatus and performing the methods of the invention. It is to be understood that the forms of the invention shown and described herein are to be considered as the presently preferred embodiments. Various changes may be made in the configurations, sizes, and arrangements of the parts of the invention, as will be recognized by those skilled in the art, without departing from the scope of the invention. For example, equivalent elements might be substituted for those illustrated and described herein, parts or connections might be reversed or otherwise interchanged, and certain features of the invention might be utilized independently of the use of other features, all as will be apparent to one of skill in the art after receiving the benefit obtained through reading of the foregoing description of the invention.

EXAMPLES

Example 1

A sheet of Valmic microporous film (25 mm v. 84 mm) was wrapped about a tow of polypropylene bulk continuous fiber and covered by a sheet of polypropylene film. The Valmic film had a mean pore size of about 0.2 micrometers and was hydrophobic to water but absorbent to nicotine. A solution of nicotine and alcohol 15-25% by weight nicotine is sprayed onto one side of the Valmic film. The film holds about 30 gm/sq.m of the nicotine solution. The polypropylene bulk tow had a fiber diameter of from 2 to 20 denier.

The nicotine dispensing device provided a pleasant draw and had suitable pressure drop characteristics. A strong nicotine sensation with no unpleasant nicotine taste was experienced by testers.

Example 2

A hollow Accurel fiber of 200 microns outside diameter was rolled into a loose ball about the size of a pea with approximately 20 to 30 other identical fibers. Nine drops of a nicotine-bearing fluid were added and the ball was massaged with Saran Wrap as protection. The fibers appeared relatively dry but totally opaque. The loose ball was stuffed inside an eight millimeter cellophane tube and assembled into the housing of a nicotine dispensing device. The device was puffed immediately with the user receiving a very strong nicotine effect with no sharp aftertaste.

After a six day storage, the sample was again tested by four individual testers who all agreed that it was the strongest nicotine "hit" they had experienced. There were no sharp painful "needles" in the mouth and throat which are normally caused by a high dosage of nicotine.

Example 3

Twenty stands of Accurel® microporous polymer fiber were purchased. Each strand was approximately 230 millimeters long. The fibers were folded in half and were soaked in a solution containing approximately one-half cubic centimeter of ethylene oxide and three drops of nicotine stabilized with propyl gallate. The bundle of fibers was thereby loaded with a nicotine bearing fluid and then hung up to dry for approximately two minutes. After that time the fibers were bone dry but contained about 40 milligrams of nicotine. The loaded bundle of microporous polymer fibers were then randomly distributed through a similarly sized selection of polypropylene tow material. The loaded fibers and polypropylene tow were assembled in a housing and the device was puffed by a variety of tasters. It was agreed that even after a substantial number of puffs the delivery was good and the delivery system was ideal.

Further modifications of the present invention will be apparent to those skilled in the art who have had the benefit of this disclosure. Such modifications however lie within the spirit and scope of the invention as defined by the following claims.

What is claimed is:

1. A nicotine dispensing device for non-pyrolytic use, said device being adapted to release nicotine-bearing vapors into air drawn through said device, said device comprising:
   (a) a housing, said housing defining a passageway for air through said device; and
   (b) a material having a plurality of microsized reservoirs containing nicotine-bearing fluid to be volatilized, said material being arranged within said housing to permit the volatilization of nicotine-bearing fluid from said material in response to suction supplied by a user.

2. The nicotine dispensing device of claim 1 wherein said housing comprises an elongated tube.

3. The nicotine dispensing device of claim 2 wherein said elongated tube includes a first portion comprising a plurality of microporous polymer filaments and a second portion usable as a mouthpiece.

4. The nicotine dispensing device of claim 1 wherein at least a portion of said housing is made from a fibrous web material.

5. The nicotine dispensing device of claim 4 wherein said fibrous web material is cigarette paper.

6. The nicotine dispensing device of claim 1 wherein said material is in the form of a film.

7. The nicotine dispensing device of claim 6 wherein said film is in a generally tubular shape.

8. The nicotine dispensing device of claim 1 wherein said material is in the form of filaments.

9. The nicotine dispensing device of claim 1 wherein said reservoirs have a mean size of less than about 10 micrometers.

10. The nicotine dispensing device of claim 1 wherein said material is microporous.

11. The nicotine dispensing device of claim 1 including a nicotine bearing fluid in said material, said fluid including a nicotine-carrier material selected from the group consisting of: menthol, freon, methyl salicylate, aldehydes, alcohols, esters, ethers, ketones, acetates, hydrocarbons and combinations thereof.

12. The nicotine dispensing device of claim 1 wherein said material is a microporous polymer.

13. The nicotine dispensing device of claim 12 wherein said microporous polymer is characterized by a relatively homogeneous, three-dimensional cellular microstructure.

14. The nicotine dispensing device of claim 12 wherein the surface of said microporous polymer material is dry to the touch after being loaded with said nicotine bearing fluid.

15. The nicotine dispensing device of claim 12 wherein said microporous polymer material is made from materials selected from the group consisting of: olefinic polymers, condensation polymers, oxidation polymers and combinations thereof.

16. The nicotine dispensing device of claim 12 wherein said microporous polymer material is made from materials selected from the group consisting of: polypropylene, polyvinyl chloride, polyethylene, cellulose acetate, cellulose triacetate, polymethylpentene, polyethylene acrylic acid, polyphenylene oxidene, styrene, polystyrene and combinations thereof.

17. An nicotine dispensing device for non-pyrolytic use, said device being adapted to release nicotine bearing vapors into air drawn therethrough, said device comprising:
   (a) a housing comprising an elongated tube, said housing defining a passageway for air through said device; and
   (b) a polymer material disposed within said housing, said material having a plurality of microsized reservoirs containing a nicotine bearing fluid to be volatilized in response to suction supplied by the user.

18. The nicotine dispensing device of claim 17 wherein said material is in the form of a microporous film.

19. The nicotine dispensing device of claim 18 wherein said film is formed into a tubular shape, the interior of said shape including an air flow restrictor.

20. The nicotine dispensing device of claim 19 wherein the surface of said material is dry to the touch after being loaded with said nicotine bearing fluid.

21. The nicotine dispensing device of claim 17 wherein said elongated tube includes a first section adapted to retain said plurality of microporous polymer filaments and a second portion adapted to be a mouthpiece.

22. The nicotine dispensing device of claim 17 wherein at least a portion of said housing is made from a fibrous web material.

23. The nicotine dispensing device of claim 22 wherein said fibrous web material is cigarette paper.

24. The nicotine dispensing device of claim 17 wherein said nicotine of said nicotine bearing fluid is selected from the group consisting of: nicotine (d), nicotine (1), nicotine (dl) nicotine salts and combinations thereof.

25. The nicotine dispensing device of claim 17 wherein said reservoirs have a mean size of less than about 10 micrometers.

26. The nicotine dispensing device of claim 17 wherein said device dispenses at least about 1 microgram of nicotine per puff.

27. The nicotine dispensing device of claim 17 wherein said material is hydrophobic.

28. The nicotine dispensing device of claim 17 comprising a nicotine-bearing fluid contained within said reservoirs, said fluid including a carrier material for said nicotine-bearing fluid selected from the group consisting of: menthol, methyl salicylate, aldehydes, alcohols, esters, ethers, ketones, acetates, hydrocarbons and combinations thereof.

* * * * *